(12) United States Patent
Timofieiev (10) Patent No.: US 12,157,020 B2
(45) Date of Patent: Dec. 3, 2024

(54) SYSTEM FOR MONITORING SERVICEABILITY STATUS PARAMETERS

(71) Applicant: DEZEGA POLSKA SP. Z O. O., Tycha (PL)

(72) Inventor: Viktor Borisovich Timofieiev, Kiev (UA)

(73) Assignee: DEZEGA POLSKA SP. Z O. O., Tycha (PL)

( * ) Notice: Subject to any disclaimer, the term of this patent is extended or adjusted under 35 U.S.C. 154(b) by 1086 days.

(21) Appl. No.: 16/964,902

(22) PCT Filed: Jan. 25, 2019

(86) PCT No.: PCT/IB2019/050620
§ 371 (c)(1),
(2) Date: Dec. 23, 2020

(87) PCT Pub. No.: WO2019/145902
PCT Pub. Date: Aug. 1, 2019

(65) Prior Publication Data
US 2021/0138278 A1    May 13, 2021

(30) Foreign Application Priority Data
Jan. 25, 2018    (PL) .......................... 424362

(51) Int. Cl.
*A62B 7/08* (2006.01)
*A62B 11/00* (2006.01)
(Continued)

(52) U.S. Cl.
CPC ................ *A62B 7/08* (2013.01); *A62B 11/00* (2013.01); *A62B 21/00* (2013.01); *H04W 4/80* (2018.02)

(58) Field of Classification Search
CPC . A62B 7/00; A62B 7/08–10; A62B 9/00–006; A62B 11/00; A62B 18/00;
(Continued)

(56) References Cited

U.S. PATENT DOCUMENTS 5,419,176 A * 5/1995 Walker ................ G01N 29/046
73/12.05
10,549,132 B2  2/2020 Murray et al.
(Continued)

FOREIGN PATENT DOCUMENTS

ZA    201301670 B    5/2014

OTHER PUBLICATIONS

Dräger Oxy 3000/6000 Mk III—How to use, 2020, Youtube, https://www.youtube.com/watch?v=en2dxuo8riE.

*Primary Examiner* — Rachel T Sippel
*Assistant Examiner* — Jacqueline M Pinderski
(74) *Attorney, Agent, or Firm* — Brian K. Yost; Decker Jones, PC (57) ABSTRACT

A method for monitoring generation of dust in a self-contained breathing apparatus involves performing a preliminary empirical compilation of databases related to an amount of dust that results from vibrations and/or mechanical impacts; determining a total empirical amplitude value; registering vibrations and/or mechanical impacts on a self-contained breathing apparatus under actual operating conditions; comparing a total breathing apparatus amplitude value with the total empirical amplitude value; generating a signal of inoperability when the dust content value exceeds a preset maximum allowable value. A monitoring device comprises a three-axis accelerometer and microcontroller configured to convert acceleration vectors into the total breathing apparatus amplitude value and compare this value the total empirical amplitude value. The device generates a (Continued)

signal of inoperability when the dust content value exceeds the preset maximum allowable value. The monitoring device may be part of a monitoring system comprising multiple breathing apparatuses and monitoring devices.

19 Claims, 3 Drawing Sheets

(51) Int. Cl.
    *A62B 21/00*     (2006.01)
    *H04W 4/80*     (2018.01)

(58) Field of Classification Search
    CPC ............ A62B 18/02–08; A62B 18/088; A62B 19/00–02; A62B 21/00; A62B 23/06; A62B 27/00; B01D 35/1435; B01D 2259/45–4541; B01D 2273/18; B01D 53/00–965; B01D 2253/00–3425; G01N 15/00; G01N 15/02; G01N 15/0255; G01N 2015/0261; G01N 2015/0096; G01N 29/045–046; G01N 29/12; G01N 2291/014; A61M 16/10–1095; G01H 13/00; H04W 4/80; G16H 40/40

See application file for complete search history.

(56) References Cited

U.S. PATENT DOCUMENTS

| | | | |
|---|---|---|---|
| 2004/0134280 A1* | 7/2004 | Hedberg | G01N 29/2418 73/578 |
| 2004/0135684 A1* | 7/2004 | Steinthal | G01N 33/0034 340/522 |
| 2007/0137491 A1* | 6/2007 | Attar | A62B 18/088 96/417 |
| 2010/0282260 A1* | 11/2010 | Sung | A61M 16/0066 128/205.12 |
| 2012/0055815 A1* | 3/2012 | Truex | A62B 27/00 206/205 |
| 2015/0217143 A1* | 8/2015 | Palmer | A62B 9/04 29/592.1 |
| 2017/0374436 A1* | 12/2017 | Awiszus | A62B 9/00 |
| 2019/0271628 A1* | 9/2019 | Littley | G01N 17/002 |

\* cited by examiner

SYSTEM FOR MONITORING SERVICEABILITY STATUS PARAMETERS

CROSS-REFERENCE TO RELATED APPLICATIONS

This application is a Section 371 (c) (1) continuation of PCT/IB2019/050620, filed Jan. 25, 2019, a continuation of PL P.424362, filed Jan. 25, 2018.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A READ-ONLY OPTICAL DISC, AS A TEXT FILE OR AN XML FILE VIA THE PATENT ELECTRONIC SYSTEM

Not Applicable.

STATEMENT REGARDING PRIOR DISCLOSURES BY THE INVENTOR OR A JOINT INVENTOR

Not Applicable.

BACKGROUND OF THE INVENTION

(1) Field of the Invention

The utility invention relates to technical means of respiratory protection to ensure human life in an unsuitable for breathing atmosphere, and it refers to a self-contained breathing apparatus with a closed respiratory system utilizing a carrier of chemically bound oxygen.

(2) Description of Related Art Including Information Disclosed Under 37 CFR 1.97 and 1.98

The self-contained breathing apparatus known as the Self-Contained Self-Rescuer (SCSR) are used in the coal mining, chemical process and other industries to protect the respiratory system from the harmful effects of toxic gases, smoke, dust, high temperature, lack of oxygen and similar ambient atmosphere factors arising from occupational accidents as well as while in space or under water.

Due to the increased requirements for safety of personnel utilizing the self-contained breathing apparatus, emphasis is given to the monitoring of parameters defining their capacity to work.

A self-contained breathing apparatus includes air circulation components contained in a tight enclosure thus eliminating the negative effect on apparatus efficiency by such environmental factors as temperature and humidity.

Regardless of the air circulation scheme used, the functioning of the known self-rescuers is based on the use of chemically bound oxygen, with potassium superoxide used for its release in regenerative cartridges as an agent for regenerating the breathing mixture.

The protective power time, which is the main criterion for self-contained breathing apparatus, depends on a number of parameters, in particular, on their aerodynamic resistance and the sorption capacity of the regenerative agent within the range of operating temperatures of the apparatus.

As a result of mechanical action during transportation and operation on self-contained breathing apparatus cartridges containing granular or palleted product with chemically bound oxygen, the granules get destroyed forming a significant amount of dust, which adversely affects the respiration physiology due to the increase of aerodynamic resistance during breathing as well as it is also unacceptable from the point of the user's health. Therefore, the intrusion of dust into the breathing circuit is strictly prohibited under the standards, and special design solutions are applied to meet these requirements.

Along with the chemical depletion of a granular or pelleted product containing chemically bound oxygen, formation of the significant amount of dust from granules or particles under the effect of mechanical stress can be an essential attribute of the regenerative cartridge efficiency.

Therefore, monitoring the amount of dust formed in the regenerative cartridge out of the particles of product with chemically bound oxygen during operation is an urgent task.

The known methods for determining the particle size composition of loose materials are only acceptable for freely moving materials, but not suitable for materials placed in a tightly sealed object.

This fact relates to the two essential aspects of the present invention determining the performance efficiency of the self-rescuer: monitoring the formation of dust and monitoring the tightness of the housing of the self-contained breathing apparatus under the influence of mechanical and climatic factors of the operation, transportation and storage environment.

A third aspect of the present invention relates to a system for monitoring efficiency parameters of multiple self-rescuers.

The included in the state of the art South African patent AA201301670 (B) (IPC: G01D. G01K; publication on 28 May 2014) only mentions the problem of fine particles of potassium superoxide, however does not develop it:

"Potassium superoxide, in either granular or pellet form, releases particles of potassium superoxide over time which often undesirably leaks into the bag of the SCSR. The bag of the SCSR is typically constructed of a material with a relatively low melting point, for example, a flexible plastic material It follows that leaked particles potassium superoxide in a heat damaged bag of an SCSR may prove to be a very undesirable and dangerous fire hazard".

Potassium superoxide, in either granular or pellet form, releases particles of potassium superoxide over time which often undesirably leaks into the bag of the SCSR. The bag of the SCSR is typically constructed of a material with a relatively low melting point, for example, a flexible plastic material It follows that leaked particles potassium superoxide in a heat damaged bag of an SCSR may prove to be a very undesirable and dangerous fire hazard.

In another document included in the state of the art, an application for an invention US2016089552 (A1) (IPC: A62B 7/08, A62B 9/00, publication on 31 Mar. 2016), there is only one phrase related to the dust generation problem: "Currently this includes a daily visual inspection of temperature and humidity indicators mounted in the case of the breathing device, verification of the manufacture date printed on the case, visual inspection for external damage to the case, and a quarterly inspection of the chemical bed using a hand held sound monitor." (Currently this includes a daily visual inspection of temperature and humidity indicators mounted in the case of the breathing device, verification of the manufacture date printed on the case, visual inspection for external damage to the case, and a quarterly inspection of the chemical bed using a hand held sound monitor.) That is to say it only speaks about identifying the presence of generated dust and a subjective assessment of its amount.

A document by Dragerwerk AG & Co. KGaA «90 41 097\4.11-4\Communications A Sales Marketing\PP\Printed in USA\Chlorine-free—environmentally compatible\Subject to modifications», 2014, mentions a transparent window in the housing of self-rescuer Drager Oxy 6000 for daily visual monitoring of fine particles of potassium superoxide: "The innovative Safety Eye is designed to let you keep an eye on safety. Providing immediate confirmation of operational readiness, this clear status window allows wearers to check for the presence of moisture and yellow KO2 fragments within the device on a daily basis". In this state of the art material there are also no technical means for unambiguous judgment on the amount of dust generated from the granules of the chemically bound oxygen carrier.

The problem of self-rescuer housing tightness monitoring is more deeply covered in the above state of the art documents.

Thus, patent ZA201301670 (B) describes a monitoring device installed in a self-rescuer sealed housing, containing a temperature sensor, a humidity sensor, a processor capable of generating alarms in case of measured temperature or humidity values go outside the predetermined ranges, recording the measured values and alarms in a memory device as well as a communication module designed for active wireless transmission of recorded data to the reading module at predetermined periodic intervals.

In the materials of patent ZA201301670 (B) there is no explanation of relation between the measured temperature and humidity values and housing tightness.

Moreover, the patent ZA201301670 (B) describes a self-rescuer safety system comprising:
  multiple self-rescuer housings equipped with monitoring devices, and
  one or more polling receiver modules or scanners for receiving alarms from multiple self-rescuer housings, each polling module being configured to signal an alarm condition if the processor is found to have generated one or more temperature or humidity alarms,
  a server containing a data collection module configured to receive information indicative of a received alarm or information indicative of a signal from multiple polling receiver modules,
  a database for data storage,
  an alarm generating module besides,
  the processor is configured to process signals from the module to generate an alarm condition in response to a request from the data acquisition module, which determines that the receiving module has received one or more alarms on changes in temperature and humidity in the self-rescuer housing.

The polling modules can be portable or fixed. The polling module can be configured to receive information from the central server indicating an emergency, usually remotely. It follows that the information indicative of an emergency condition received by the polling receiving module includes information indicative of the housing that may be faulty in order to enable the operator of the polling receiving module to remove such self-rescuer.

Moreover, the patent ZA201301670 (B) describes a self-rescuer monitoring method comprising such steps: receiving one or more of a temperature alarm flag indicative of an unacceptable temperature value being determined within or outside a particular SCSR housing, a humidity alarm Hag indicative of an unacceptable humidity level being determined within the SCSR housing, and a working Hag indicative of an acceptable temperature value being determined within or outside the SCSR housing and an acceptable humidity level being determined within the SCSR housing; and generating an alarm in response to receiving one or more of the temperature or humidity alarm flag from the SCSR housing.

(31. A method for monitoring self-contained self-rescuers (SCSRs), the method comprising the steps of
  receiving one or more of a temperature alarm flag indicative of an unacceptable temperature value being determined within or outside a particular SCSR housing, a humidity alarm flag indicative of an unacceptable humidity level being determined within the SCSR housing, and a working flag indicative of an acceptable temperature value being determined within or outside the SCSR housing and an acceptable humidity level being determined within the SCSR housing, and
  generating an alarm in response to receiving one or more of the temperature or humidity alarm flag from the SCSR housing.)

According to this monitoring method, the processor of the monitoring device is nominally in 3 "sleep" mode, it is activated at specified time intervals to measure temperature and humidity values and to record the measured values into non-volatile memory as well as to actively transmit measured values and/or alarms via a wireless channel to the polling module, and then transfers into the "sleep" mode to save power Data transmission can also be activated under the request from the polling module.

Another included in the state of the art document—application for an invention US2016089552—describes a breathing apparatus comprising: a case containing at least a chemical for generating oxygen; and a monitoring circuit within the case, the monitoring circuit including a plurality of sensors configured to sense parameters within the case relevant to an operational status of the breathing apparatus, and a controller configured to receive signals from the sensors and to produce an output signal indicating the operational status of the breathing apparatus.

(1. A breathing apparatus comprising:
  a case containing at least a chemical for generating oxygen; and
  a monitoring circuit within the case, the monitoring circuit including a plurality of sensors configured to sense parameters within the case relevant to an operational status of the breathing apparatus, and a controller configured to receive signals from the sensors and to produce an output signal indicating the operational status of the breathing apparatus.)

The method for monitoring a breathing apparatus described in the above application comprises: using a plurality of sensors within a case of a breathing apparatus to sense parameters relevant to an operational status of the breathing apparatus; and processing signals from the sensors to produce an output signal representative of the operational status of the breathing apparatus.

(7. A method for monitoring a breathing apparatus, the method comprising using a plurality of sensors within a case of a breathing apparatus to sense parameters relevant to an operational status of the breathing apparatus, and processing signals from the sensors to produce an output signal representative of the operational status of the breathing apparatus.)

The application describes the value of housing lightness for ensuring operating efficiency of the self-rescuer. but it lacks criteria for processing signals from the sensors for its monitoring.

BRIEF SUMMARY OF THE INVENTION

The objective of the invention is to improve reliability of self-rescuers by using means for monitoring parameters that determine their performance. The set task is solved by the features of independent points of the invention formula. Further on, the features and advantages of the invention are explained in detail by way of an example using a figure depicting a block diagram of the monitoring system. Two aspects of the present invention relate to: 1. determining the performance efficiency of the self-rescuer and 2. monitoring the formation of dust and the tightness of the housing of the self-contained breathing apparatus under the influence of mechanical and climatic factors of the operation, transportation and storage environment. A third aspect of the present invention relates to a system for monitoring efficiency parameters of multiple self-rescuers.

DETAILED DESCRIPTION OF THE INVENTION

Figure 2:
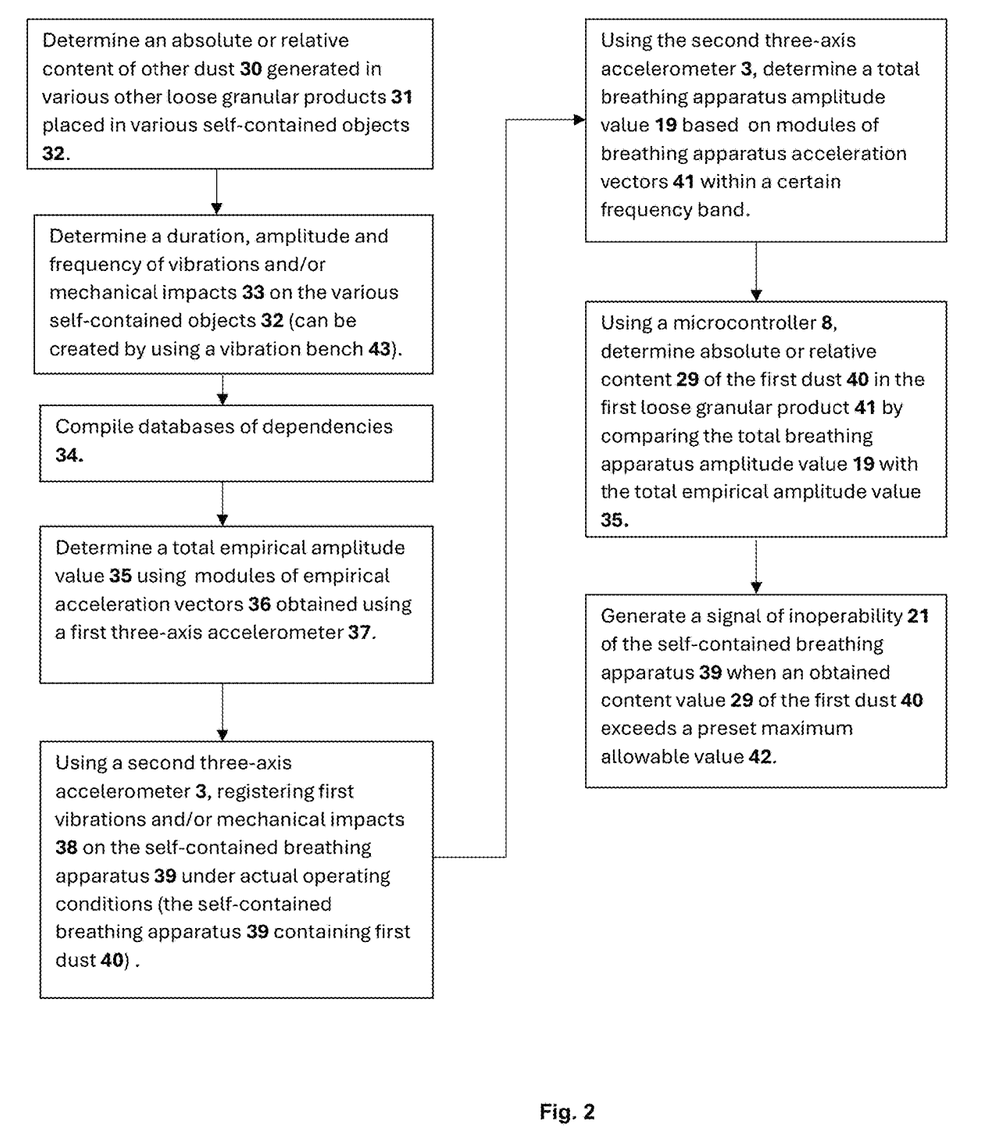
FIG. 2 is a flow diagram of a method for monitoring the generation of dust, in accordance with a preferred embodiment.

Concerning the first aspect of the invention, a method has been developed for monitoring the generation of dust from loose granular product under the influence of mechanical loads, which involves the creation of dust generation databases 34, which were previously empirically compiled for various designs of self-rescuers, and containing dependences of the absolute or relative content of dust 30 generated from various loose granular products 31 placed in various self-contained self-rescuers 32, caused by mechanical impacts 33, which type and parameters (shock, vibration, duration, amplitude and frequency range) are similar to the real operating conditions of self-rescuers.

For this purpose, the specified mechanical effects are created using a vibration bench 43, on which the tested self-rescuer 32 with loose granular carrier of chemically bound oxygen is installed.

According to the invention, a model of accumulation of the sum of the amplitudes of the acceleration vectors modules of individual oscillations is adopted as a universal measure for the level of various types of mechanical stress. Vibrations are recorded using a first three-axis accelerometer 37 with a shock load sensor function.

Thus, when creating the mentioned databases 34, the relative or absolute amount of dust 30 formed from the carrier of chemically bound oxygen is determined by the method of granulometric analysis at various values of mechanical stresses produced by the vibration bench 43 with a certain pitch in the form of the total amplitude value of the acceleration vectors 36. When forming these dependencies, the maximum permissible total amplitude value of acceleration vectors 35 corresponding to the maximum permissible dust content in the cartridge with loose granular product is also determined.

On the basis of these databases, during self-rescuers' operation, transportation and storage, the absolute or relative content of dust 40 in loose granular product is determined by way of comparing the total amplitude value of mechanical stresses on the self-rescuer housing 19 with the respective empirical dependence 35. At that, monitoring of vibrations 38 in the self-rescuer is also performed using a three-axis accelerometer 3.

Figure 3:
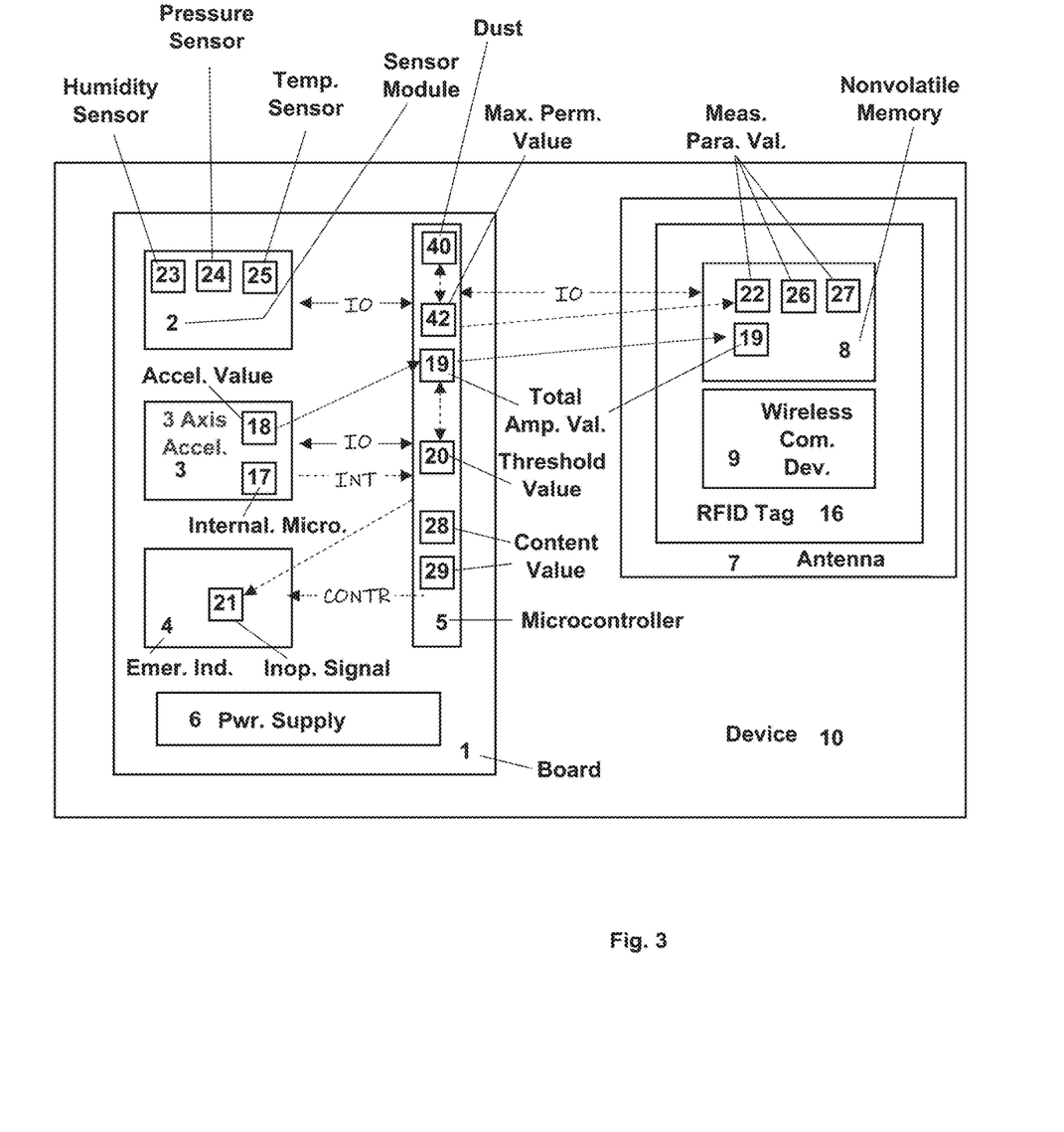
FIG. 3 is a block diagram of the monitoring device of the present invention, in accordance with a preferred embodiment.

To implement the described above method for monitoring dust generation according to the invention, a device 10 is proposed for monitoring dust generation to be installed in the self-rescuer 39, which main functional elements are a three-axis accelerometer 3, a microcontroller 5, a non-volatile memory device 8 and a wireless communication device 9.

The three-axis accelerometer used in the monitoring device is made in the form of a MEMS (Microelectromechanical systems) microchip. It contains an internal microprocessor 17 capable of generating acceleration values 18 along all three axes and interrupt signals for shock load events exceeding predetermined threshold values 20 of acceleration amplitude, exposure time, frequency band. The specified threshold values 20 are received by the wireless communication device, written into the non-volatile memory and, upon a command by the microcontroller, transferred to the memory of the internal accelerometer microprocessor.

In the process of forming the dust generation database or during the actual operation of self-rescuer 39, for monitoring dust 40 formation based on the signals generated by the accelerometer 3, the microcontroller of the device calculates the amplitude value of the acceleration vector of an individual vibration as the square root of the sum of squares of the acceleration values along all three axes X, Y, Z, and forms the sum of the amplitude values of acceleration vectors of vibrations to which the accelerometer is subjected. Since the accelerometer 3 is an integral pan of the dust generation monitoring device installed in the self-rescuer 39, and the cartridge with the chemically bound oxygen carrier is permanently mounted in the body of the self-rescuer, the resulting total amplitude value 19 corresponds to the total mechanical impact 38 and, according to the invention, to the amount of dust 40 generated from panicles of the granular chemically bound oxygen carrier.

In the course of actual operation of the self-rescuer, on the basis of shock events, the microcontroller records the calculated total amplitude value 19 into the non-volatile memory, provides it for reading via a wireless communication device as a value that determines the operation life of the self-rescuer against the dust generation criterion, and compares it with the maximum permissible value 42 obtained through a wireless communication device and stored in non-volatile memory.

When the calculated total amplitude value 19 exceeds the maximum permissible value 42, the microcontroller generates a signal of the self-rescuer inoperability, writes it to the memory device, and activates the alarm indicator of the self-rescuer.

In the preferred embodiment of the invention, the non-volatile memory 8 and the wireless communication device 9 are made in the form of a semi-active RFID tag 16 equipped with an antenna 7, which only consumes energy from a self-contained power supply for the operation of the microcontroller to perform calculations, control the accelerometer and write data to the memory device. Reception and transmission of external data is performed at the expense of energy received by RFID tag antenna from the reader device 11, due to which the life time of the self-contained power supply is at least 10 years, which significantly exceeds the life time of state of the art analogues containing active RFID tags.

Availability of such a tool for quantitative determination of dust content in loose granular carrier of chemically bound oxygen allows determining the operating lifetime and correctly planning the operation and maintenance of the self-rescuer.

The described above method and device can be used both separately for implementation of the first aspect of the invention—monitoring of dust generation in various devices, and for the joint implementation of the first two above-mentioned aspects of the invention by way of integrating into the method and device for integrated monitoring of the performance parameters of various devices and systems in various areas of industry and in everyday life.

The respective to the invention method for integrated monitoring of the parameters of operability status of a tight self-contained self-rescuer containing loose granular earner of chemically bound oxygen involves measuring the same parameters of operation, transportation and storage conditions as in state of the art materials: temperature, humidity and pressure inside the self-rescuer, mechanical vibration and impact effects on the self-rescuer. The difference from the state of the art consists in the processing of measured parameters.

The measured values are used to generate the inoperability signal(s) based on the criteria listed below, the sequence of their presentation is not related to their priority (significance). During the self-rescuer operation, a variety of combinations of conditions determining its performance can develop To improve the reliability of monitoring, the method is based on various criteria, for each of which an inoperability signal 21 can be generated independently, and for the subsequent analysis of the causes it is provided that the data of the non-volatile memory corresponding to the inoperability sign contains bit fields with specific criteria that caused the inoperability.

The performance of self-rescuer is affected by external climatic parameters, primarily temperature. Since the housing of the self-rescuer has high thermal conductivity, the external temperature affects the interior of the self-rescuer with only an insignificant delay. The actual operating temperature of the self-rescuer ranges from −40° C. to +70° C. With prolonged exposure to a higher temperature, destruction of internal components and parts begins resulting in self-rescuer inoperability. Hence, the first criterion of inoperability follows: exposure to temperature above a given value for a certain time.

It is commonly known that release of oxygen from the granular regenerative product contained in the cartridge is driven by moisture during exhalation. In case of loss of tightness of the housing, environmental moisture penetrates inside resulting the decrease of the protective action time under the prolonged exposure to moisture. This is the basis for the second criterion of inoperability—the exposure to absolute humidity above a given value for a certain time.

An essential feature characterizing the housing tightness is the thermodynamic constant, the so-called isochore, which is calculated by dividing the current pressure value by the current temperature value.

To detect leaks in the self-rescuer housing, in contrast to analogs that analyze directly measured values of climatic parameters inside the self-rescuer housing, under the invention, the gradients of the measured values of humidity, temperature, absolute pressure, as well as isochores, that is, the rate of their change, are calculated, which increases the sensitivity of detecting their critical changes due to loss of tightness.

The integrated monitoring method according to the invention also includes a method for dust generation monitoring performed in accordance with claim 1 of the patent claims.

The device implementing the described method of integrated monitoring is made in the form of a structurally complete module suitable for installation on or in a self-rescuer. It includes dust generation monitoring device elements according to claim 6 of the patent claims.

The presented in the figure device 10 for integrated monitoring of the self-rescuer performance contains a board 1, on which environmental parameters sensor module 2 is installed with sensors 23, 24, 25, for measuring relative humidity (humidity sensor 23), absolute pressure (pressure sensor 24) and temperature (temperature sensor 25), a three-axis accelerometer 3 with the function of an impact stress sensor, an emergency indicator 4, a microcontroller 5 and a self-contained power supply source 6 as well as an antenna 7 with an RFID tag installed on it, containing a non-volatile storage device 8 and a transceiving RFID module 9. The microcontroller 5 and RFID tag are connected via digital 10 interface.

Via the RFID interface, microcontroller 5 receives the setting data from reader 11, via digital input-output interfaces it sets up the sensors and, based on the measured values, implements the integrated monitoring algorithms set forth in the method. In doing so, it uses the interrupts (INT) generated in the three-axis accelerometer 3.

Microcontroller 5 writes the current values of measured parameters into the non-volatile memory 8, from which they can be read by reader 11 via the RFID interface.

In the event of generation of inoperability signal, microcontroller 5 writes data on the inoperability into the non-volatile memory 8, and controls the alarm indicator 4 via the CONTR line.

The device 10 for integrated monitoring can be used both for autonomous monitoring of the self-rescuer's performance using only the built-in emergency indicator 4, and as part of a monitoring system for multiple self-rescuers.

A third aspect of the present invention relates to a system for monitoring efficiency parameters of multiple self-rescuers.

The include in the state of the art monitoring system is limited to a single local server for collecting data from multiple reader devices, each of which receives data from a plurality of self-rescuers operating at the same location, for example, a mine, a factory, etc.

The monitoring system according to the present invention involves monitoring all the manufacturer's self-rescuers used at different plants and even in different countries, and covers an international network of local servers.

Figure 1:
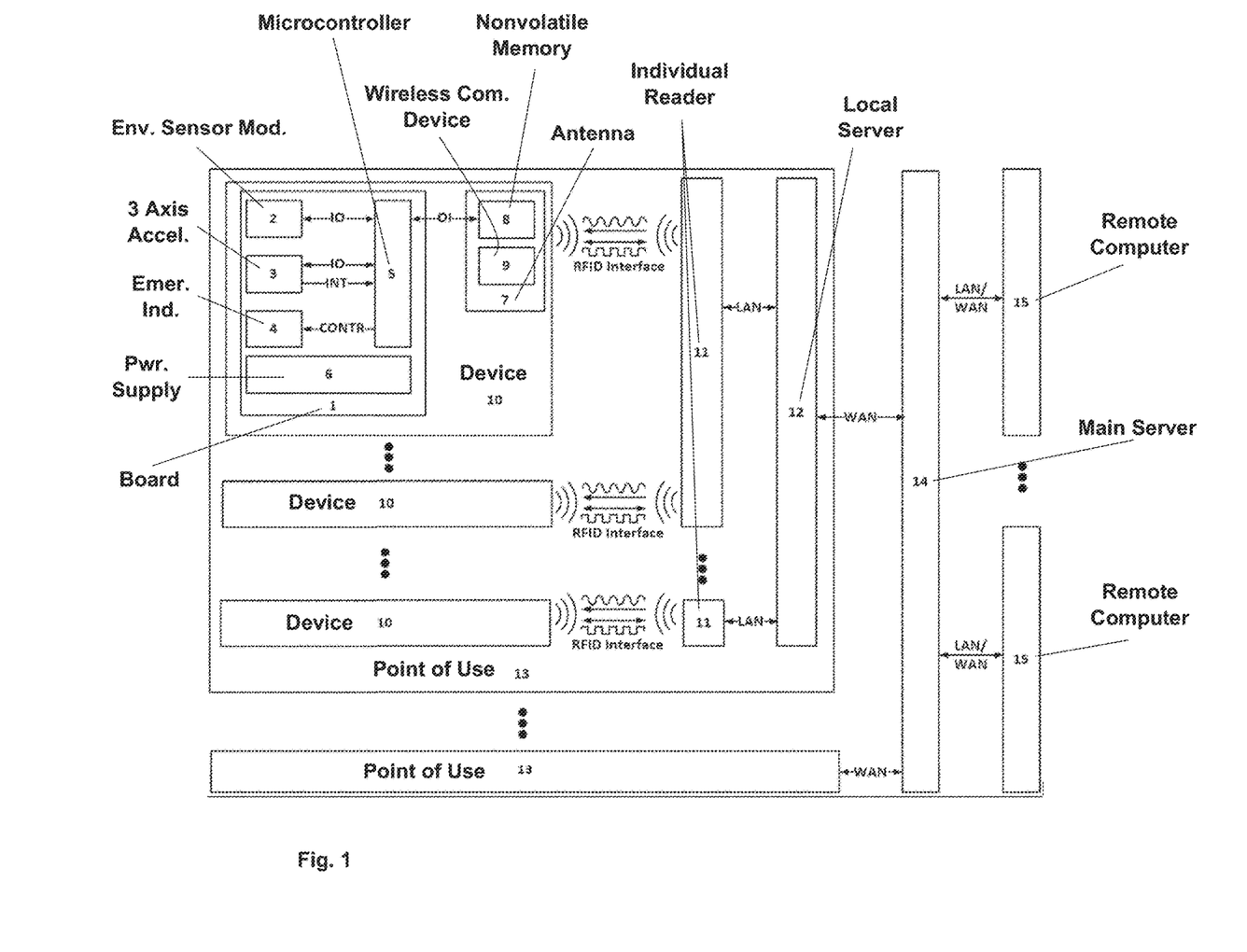
FIG. 1 is a block diagram of systems and components of the present invention in accordance with a preferred embodiment.

FIG. 1 shows a block diagram of an embodiment of a monitoring system covering a plurality of spaced-apart points of use 13, each having at least one local server 12 is installed, connected via a local computer network to at least one reader 11, which is connected via a wireless channel with at least one device 10 for integrated monitoring of the parameters of self-rescuer operability status, installed on a self-rescuer or in a self-rescuer 39.

The local servers 12 are connected to the main server 14 via a local area network or, for example, the Internet.

Local servers 12 generate requests to receive data from all reading devices 11 connected to the local area network. Local servers 12 periodically transfer the accumulated data to the main server.

Main server 14 contains the main database of all manufactured self-rescuers, which is formed on the basis of the manufacturer's data as well as monitoring data obtained from local servers 12 during the operation of the self-rescuers.

The database on the main server 14 contains information about types, serial numbers, distribution of self-rescuers among local servers 12 and specific points of operation 13, monitoring parameters linked to real time, statistics on the use of self-rescuers, their operating lifetime, a list of repair and maintenance works.

Remote computer 15 has the ability to analyze the database on the main server 14 and control the individual readers 11 at the points of use 13. To implement different capabilities of remote computers, different access rights of remote computers to the database on the main server are used.

The invention claimed is:

1. A method for monitoring generation of a first dust from particles of a first loose granular product with a regular and/or irregular structure placed in a self-contained breathing apparatus under an influence of first vibrations and/or mechanical impacts, the method comprising the steps of:
  a) performing a preliminary empirical compilation of databases of dependencies of an absolute or relative content of respective other dust generated in respective various other loose granular products placed in various respective self-contained objects, on a duration, amplitude and frequency of a plurality of respective other vibrations and/or mechanical impacts on the respective various self-contained objects, so as to determine a total empirical amplitude value, the total empirical amplitude value being determined by using modules of empirical acceleration vectors, the modules of empirical acceleration vectors obtained using a first three-axis accelerometer;
  b) using a second three-axis accelerometer, registering the first vibrations and/or mechanical impacts on the self-contained breathing apparatus under actual operating conditions and determining a total breathing apparatus amplitude value, the total breathing apparatus amplitude value being determined by using modules of breathing apparatus acceleration vectors within a certain frequency band, the modules of breathing apparatus acceleration vectors obtained using the second three-axis accelerometer;
  c) using a microcontroller, determining an absolute or relative content value of the first dust in the first loose granular product by comparing the total breathing apparatus amplitude value with the total empirical amplitude value;
  d) generating a signal of inoperability of the self-contained breathing apparatus when the determined absolute or relative content value of the first dust exceeds a preset maximum allowable value;
  wherein the self-contained breathing apparatus comprises a monitoring device, the monitoring device comprising:
  the second three-axis accelerometer and the microcontroller, the microcontroller being operatively connected to the second three-axis accelerometer;
  a non-volatile memory device operatively connected to the microcontroller;
  a wireless communication device, an alarm indicator, and a self-contained power supply;
  the non-volatile memory device and the wireless communication device forming a semi-active radio-frequency identification (RFID) tag;
  the microcontroller configured to convert the modules of breathing apparatus acceleration vectors received from the second three-axis accelerometer into the total breathing apparatus amplitude value;
  the microcontroller further configured to record the total breathing apparatus amplitude value and the total empirical amplitude value in the memory device and generate the signal of inoperability.

2. The method according to claim 1, further comprising the steps of:
  creating a plurality of respective measured values by:
    measuring temperature, humidity, and pressure inside the self-contained breathing apparatus; and
    measuring the vibrations and/or mechanical impacts on the self-contained breathing apparatus:
  storing the respective measured values in the non-volatile memory device in real time;
  comparing the respective measured values against respective preset permissible values;
  generating an alarm signal when at least one of the plurality of respective measured values is outside at least one of the respective preset permissible values;
  storing inoperability data in the non-volatile memory device when at least one of the plurality of respective measured values is outside at least one of the respective preset permissible values, the inoperability data comprising information related to the plurality of respective measured values in relation to the respective reset permissible values;
  transmitting the alarm signal via a wireless communication channel to a data collection device.

3. The method according to claim 1, wherein the first and the various other loose granular products comprise a chemically bound oxygen carrier in the form of granules or pellets.

4. The method according to claim 1, wherein the plurality of respective other vibrations and/or mechanical impacts are implemented by using a vibration bench.

5. The method according to claim 1, wherein the second three-axis accelerometer is installed on or in the self-contained apparatus.

6. A device for monitoring generation of dust from particles of a loose granular product placed in a tightly sealed object, the device comprising:
  a three-axis accelerometer and a microcontroller operatively connected to the three-axis accelerometer;
  a non-volatile memory device operatively connected to the microcontroller;
  a wireless communication device, an alarm indicator, and a self-contained power supply;
  the non-volatile memory device and the wireless communication device forming a semi-active radio-frequency identification (RFID) tag;

the microcontroller configured to convert acceleration vector values received from the three-axis accelerometer into a total amplitude signal of acceleration vector value;

the microcontroller further configured to:
record the total amplitude signal of acceleration vector value into the non-volatile memory device;
compare the total amplitude signal of acceleration vector value with a maximum permissible value recorded in the non-volatile memory device;
generate a signal of inoperability of the tightly sealed object when the maximum permissible value is exceeded;
record signal of inoperability in the non-volatile memory device; and
activate the alarm indicator.

7. The device according to claim 6, wherein the three-axis accelerometer comprises micro-electromechanical system (MEMS) technology and an internal microprocessor capable of generating acceleration vector values and interrupt signals, the acceleration vector values and interrupt signals being related to vibrations and/or mechanical impacts exceeding predetermined threshold values.

8. The device according to claim 6, wherein the device is a structurally complete module suitable for installation on or in a self-contained breathing apparatus.

9. A method for integrated monitoring of parameters of an operability state of a self-contained breathing apparatus containing a loose granular product, the method comprising the steps of:
creating a plurality of respective measured values by:
using environmental sensors, measuring temperature, humidity, and pressure inside the self-contained breathing apparatus; and
using a three-axis accelerometer, measuring vibrations and/or mechanical impacts on the self-contained breathing apparatus;
the plurality of respective measured values comprising a measured temperature value and a measured humidity value;
the respective preset permissible values comprising a preset maximum temperature value and a preset maximum humidity value;
storing the respective measured values in a non-volatile memory device in real time;
comparing the respective measured values against respective preset permissible values;
calculating a thermodynamic constant isochore value;
using the measured values, calculating a dust content value, the dust content value being an amount of dust generated from particles of the loose granulated product;
generating an alarm signal when at least one of the plurality of respective measured values is outside at least one of the respective preset permissible values or when the calculated thermodynamic constant isochore value exceeds a predetermined isochore value limit or upon the dust content value exceeding a predetermined dust content value;
storing inoperability data in the non-volatile memory device when at least one of the plurality of respective measured values is outside at least one of the respective preset permissible values, the inoperability data comprising information related to the plurality of respective measured values in relation to the respective preset permissible values;

transmitting alarm signal via a wireless communication channel to a data collection device;
wherein the self-contained breathing apparatus comprises a monitoring device, the monitoring device comprising:
the three-axis accelerometer and a microcontroller, the microcontroller being operatively connected to the three-axis accelerometer;
the non-volatile memory device, the non-volatile memory device being operatively connected to the microcontroller;
a wireless communication device, an alarm indicator, and a self-contained power supply;
the non-volatile memory device and the wireless communication device forming a semi-active radio-frequency identification (RFID) tag.

10. The method of claim 9, wherein:
the alarm signal being generated when the measured temperature value exceeds the preset maximum temperature value during a first specified time interval or when the measured humidity value exceeds the preset maximum humidity value during a second specified time interval.

11. The method of claim 10,
wherein:
the alarm signal is generated upon a loss of tightness of the tightly sealed object resulting from:
at least one of the plurality of respective measured values being outside at least one of the respective preset permissible values; or
the A the thermodynamic constant isochore value exceeding the predetermined isochore value limit;
or the dust content value exceeding a predetermined dust content value.

12. The method of claim 11, wherein:
the step of measuring vibrations and/or mechanical impacts on the tightly sealed object is carried out at a given frequency and/or at interruptions from the three-axis accelerometer corresponding to the vibrations and/or mechanical impacts;
A the step of calculating the thermodynamic constant isochore value is performed by dividing a current pressure value by a current temperature value.

13. A device for integrated monitoring of status parameters of a tightly sealed object containing loose granular product, the device comprising:
a temperature sensor, a humidity sensor, a pressure sensor, and a three-axis accelerometer;
a microcontroller operatively connected to the temperature sensor, the humidity sensor, the pressure sensor, and the three-axis accelerometer;
a non-volatile memory device;
a wireless communication device;
an alarm indicator;
a self-contained power supply;
the microcontroller configured to be capable of:
a. performing measurements at a given frequency and/or at interruptions from the three-axis accelerometer corresponding to impact events;
b. determining a dust content, the dust content being an amount of dust generated from particles of the loose granular product under an effect of mechanical loads, the dust content being determined by using a total amplitude value of acceleration vectors received from the three-axis accelerometer;
c. calculating a value of a thermodynamic constant isochore by dividing a current pressure value by a current temperature value;

d. calculating respective gradients of measured values of humidity, temperature, and absolute pressure;
e. calculating an isochore gradient;
generating an alarm signal of inoperability
f. when:
 1. the measured temperature value exceeds a specified maximum permissible temperature value during a first specified time interval; or
 when the measured humidity value exceeds a specified maximum permissible humidity value during a second specified time interval;
 2. or
 3. when the determined dust content exceeds a predetermined dust content value; or
 when
 4. at least one of the respective gradients of measured values and the isochore gradient exceed respective predetermined gradient values;
g. the microcontroller being further configured to be capable of generating inoperability data in the non-volatile memory, the inoperability data relating to causes of inoperability of the device.

14. The device according to claim 13, further comprising an environmental sensor module, the environmental sensor module comprising the humidity sensor, the pressure sensor, and the temperature sensor.

15. The device according to claim 13, wherein a semi-active radio-frequency identification (RFID) tag comprises the non-volatile memory and the wireless communication device.

16. The device according to claim 13, wherein the device is suitable for installation on or in the tightly sealed object.

17. The device according to claim 13, wherein the tightly sealed object is a self-contained breathing apparatus containing a granular carrier of chemically bound oxygen.

18. A system for monitoring respective performance status parameters of a plurality of respective tightly sealed objects containing respective loose granular product, the system comprising:
 at least one respective monitoring device installed on or in each of the respective tightly sealed objects, each of the respective monitoring devices being capable of monitoring the respective performance status parameters of the respective tightly sealed objects;
 at least one respective mobile or fixed wireless reader communicatively connected to the respective monitoring device via a respective wireless channel, the respective reader being communicatively connected by a first local area network to at least one monitoring data collection device comprising a local server;
 a main server communicatively connected to the local server via the first local area network or a global computer network;
 the main server communicatively connected to a remote computer via a second local area network or the global computer network;
 a main database, the main database comprising object, the object data being information related to the tightly sealed objects, the object data capable of being generated on the main server and comprising manufacturer's data and monitoring data capable of being obtained from the local server during an operation of the tightly sealed objects;
 each of the respective monitoring devices comprising:
  a temperature sensor, a humidity sensor, a pressure sensor, and a three-axis accelerometer;
  a microcontroller operatively connected to the temperature sensor, the humidity sensor, the pressure sensor, and the three-axis accelerometer;
  a non-volatile memory device;
  a wireless communication device;
  an alarm indicator;
  a self-contained power supply;
  the microcontroller configured to be capable of:
   a. performing measurements at a given frequency and/or by interruptions from the three-axis accelerometer corresponding to impact events;
   b. determining a dust content, the dust content being an amount of the dust generated from particles of the loose granular product under an effect of mechanical loads, the dust content being determined by using a total amplitude value of acceleration vectors received from the three-axis accelerometer;
   c. calculating a value of a thermodynamic constant isochore by dividing a current pressure value by a current temperature value;
   d. calculating respective gradients of measured values of humidity, temperature, and absolute pressure;
   e. calculating an isochore gradient;
   f. generating an alarm signal of inoperability when:
    1. the measured temperature value exceeds a specified maximum permissible temperature value during a first specified time interval; or
    2. when the measured humidity value exceeds a specified maximum permissible humidity value during a second specified time interval; or
    3. when the determined dust content exceeds a predetermined dust content value; or
    4. when at least one of the respective gradients of measured values and the isochore gradient exceed respective predetermined gradient values;
   g. the microcontroller being further configured to be capable of generating inoperability data in the non-volatile memory, the inoperability data relating to causes of inoperability of the respective monitoring device.

19. The system according to claim 18, wherein each of the plurality of tightly sealed objects is a self-contained breathing apparatus and wherein the loose granular product is a granular carrier of chemically bound oxygen.

* * * * *